United States Patent
Svarczkopf

(10) Patent No.: US 11,953,489 B1
(45) Date of Patent: *Apr. 9, 2024

(54) EVALUATING SPONTANEOUS HYDRAULIC FRACTURING FLUID IMBIBITION AND OIL DISPLACEMENT METHOD AND APPARATUS

(71) Applicant: Imperative Chemical Partners, Inc., Midland, TX (US)

(72) Inventor: Timothy C Svarczkopf, Midland, TX (US)

(73) Assignee: Imperative Chemical Partners Inc., Midland, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/375,775

(22) Filed: Jul. 14, 2021

Related U.S. Application Data

(63) Continuation of application No. 17/238,746, filed on Apr. 23, 2021, now Pat. No. 11,092,586.

(60) Provisional application No. 63/028,742, filed on May 22, 2020.

(51) Int. Cl.
| | |
|---|---|
| *G01N 33/24* | (2006.01) |
| *E21B 43/26* | (2006.01) |
| *E21B 49/02* | (2006.01) |
| *G01N 15/08* | (2006.01) |

(52) U.S. Cl.
CPC ............ *G01N 33/241* (2013.01); *E21B 49/02* (2013.01); *G01N 15/0826* (2013.01); *E21B 43/26* (2013.01)

(58) Field of Classification Search
CPC .... G01N 19/00; G01N 33/24; G01N 33/2823; G01N 1/34; G01N 1/4077; G01N 15/08; G01N 2001/4083; G01N 24/081; G01N 33/241; E21B 43/26; E21B 43/16
See application file for complete search history.

(56) References Cited

U.S. PATENT DOCUMENTS

| | | | |
|---|---|---|---|
| 2013/0014561 A1* | 1/2013 | Anderson .............. | G01N 33/24 73/38 |
| 2022/0291157 A1* | 9/2022 | Yao ........................ | G01N 33/24 |

FOREIGN PATENT DOCUMENTS

| | | | | |
|---|---|---|---|---|
| CN | 109001097 A | | 12/2018 | |
| CN | 208520730 U | * | 2/2019 | ........... G01N 15/082 |

\* cited by examiner

*Primary Examiner* — Harshad R Patel
*Assistant Examiner* — Gedeon M Kidanu
(74) *Attorney, Agent, or Firm* — Phillips Murrah PC; Martin G. Ozinga

(57) ABSTRACT

The present invention comprises a test for evaluating spontaneous hydraulic fracturing fluid imbibition and oil displacement method and apparatus utilizing a composite core with a pressurized Amott cell test.

1 Claim, 2 Drawing Sheets

EVALUATING SPONTANEOUS HYDRAULIC FRACTURING FLUID IMBIBITION AND OIL DISPLACEMENT METHOD AND APPARATUS

CROSS-REFERENCE TO RELATED APPLICATIONS

This present patent application is a continuation of U.S. patent application Ser. No. 17/238,746 filed on Apr. 23, 2021, currently pending, in which priority is claimed from U.S. Provisional Patent Application Ser. No. 63/028,742 filed on May 22, 2020. Each of the applications listed above is expressly incorporated herein by reference in their entirety.

BACKGROUND OF THE INVENTION

1. Field of the Invention

In general, the present invention relates to oil and gas well fracturing. More particularly, the present invention provides an apparatus, system, and method for evaluating spontaneous hydraulic fracturing fluid imbibition and oil displacement utilizing a composite core with a pressurized Amott cell test.

2. Description of the Prior Art

The fracturing fluids used for gas shale stimulations consist primarily of water but also include a variety of additives. The number of chemical additives used in a typical fracture treatment varies depending on the conditions of the specific well being fractured. The predominant fluids currently being used for fracture treatments in the oil and gas shale plays are water-based fracturing fluids mixed with friction-reducing additives called slickwater. The addition of friction reducers allows fracturing fluids and proppant to be pumped to the target zone at a higher rate and reduced pressure than if water alone were used.

Because the make-up of each fracturing fluid varies to meet the specific needs of each area, there is no one-size-fits-all formula for the volumes for each additive. In classifying fracturing fluids and their additives, it is important to realize that service companies that provide these additives have developed a number of compounds with similar functional properties to be used for the same purpose in different well environments. The difference between additive formulations may be as small as a change in concentration of a specific compound.

Fracturing fluid chemical composition can be utilized as a lever for increasing well productivity. Changes to fracturing fluid chemistry have been proven to increase well EUR's by 42% or more. Fracturing fluids may need to be comprised of dozens of chemical components in order to increase well productivity. Therefore, it is crucial that there is a test method that allows for measurement of the ability of a holistic fracturing fluid and/or individual components to interact with unconventional shale oil and gas resource rocks to improve upon the wettability and subsequent fluid imbibition and oil displacement mechanism in those rocks.

Amott cell imbibition and drainage apparatus and methods utilizing core were developed for conventional sandstones that are 500 millidarcies to 2.5 darcies in permeability. The methods and apparatus are not effective for 100 nanodarcies to 10 millidarcies permeability rocks that characterize unconventional oil and gas shale resources. The problems with existing Amott cell imbibition/drainage apparatus and methods are exacerbated by higher concentrations of swelling and migrating clays in unconventional shale oil and gas resource rocks. Clay wetting can overstate the actual wetting a fluid can achieve in the actual practice of hydraulic fracturing. Pressure forces in hydraulic fracturing cause fines migration and fouling of pore spaces that simply cannot be observed in a static Amott cell experiment.

Prior art utilizing core in Amott cells for the purpose of measuring imbibition of a particular fluid and subsequent oil displacement is evidenced in offerings by Vinci Technologies and PanTerra Consultants. Deficiencies in both Vinci, Panterra, and other forms of atmospheric prior art are similar or the same.

The prior art cells and methods are not capable of simulating the pressure forces that unconventional shale oil and gas resource rocks undergo when hydraulically fractured. The cells are limited to 30 PSI pressure, which is very close to the maximum pressure that glass can withstand. Unconventional shale oil and gas resource rock wells have imbibition pressure forces that can be in the range of 250 PSI to 5000 PSI greater than the confining pressure.

The prior art failure to provide imbibition pressure forces similar to those experienced in hydraulic fracturing operations results in a failure to account for fines migration and fouling of pore throats in the imbibing step.

The prior art exaggerates the imbibition drive created by clays, which can absorb up to seven times their weight in water and thus overstates the imbibition drive of the fluid itself.

The prior art takes as long as 30 days for the fluid to be imbibed into the core and cause the oil in the core to be displaced making it impossible to evaluate hundreds to thousands of fluid combinations.

The prior art requires that cores be saturated with oil using a pump prior to spontaneous imbibition and oil displacement experiments. The process of pumping oil into the core to saturate it creates gas solubility, gas compression, and fines mobilization issues that result in a lack of reproducibility of the experimental results.

The prior art requires use of native core, which is not readily available resulting in lack of a statistically significant population of sample.

Additional prior art for evaluating imbibition of a fluid and subsequent oil displacement utilizing core is represented in a technical paper titled "Oil recovery and wettability alteration in carbonates due to carbonate water injection" by Ruidiaz, Winter, and Trevisan. The paper vaguely describes a pressure cell for spontaneous imbibition but there are several flaws with the method:

Millidarcy permeability carbonate rock cores are used in the testing as opposed to nanodarcy shale cores. Cores get cleaned with distilled water prior to experimentation. This water would react with any clays present in shale oil and gas reservoir rock causing significant errors to reproducibility. Cores get saturated with oil by pumping the oil into the core at 2000 PSI. The process of pumping oil into the core to saturate it creates gas solubility, gas compression, and fines mobilization issues that result in a lack of reproducibility of the experimental results. It takes 24 hours to saturate the core with the oil pump. The test method requires aging from 42 to 104 days, which precludes the possibility of analyzing hundreds to thousands of possible fluid combinations. Prior art requires use of native core, which is not readily available resulting in lack of a statistically significant population of sample.

Additional prior art for evaluating imbibition of a fluid and subsequent oil displacement utilizing core is represented in a technical paper titled "A Novel Enhanced Oil Recovery Technology Using Dimethyl Ether/Brine: Spontaneous Imbibition in Sandstone and Carbonate Rocks" by Chahardowli etal. Some flaws with the method and apparatus relative to use for unconventional shale oil and gas resource rocks are:

Millidarcy permeability carbonate and sandstone cores are used in the testing as opposed to nanodarcy shale cores. The apparatus and method was limited to 9 bars or 130 PSI. This imbibition drive pressure is much lower than that which is experienced in hydraulic fracturing. The apparatus and method was designed for dissolving a gas into a fluid and creating a forced imbibition experiment with that as opposed to being designed for a hydraulic fracturing fluid. Cores get saturated with oil by pumping the oil into the core at an undefined pressure. The process of pumping oil into the core to saturate it creates gas solubility, gas compression, and fines mobilization issues that result in a lack of reproducibility of the experimental results. The pressure cell was only 8 cm long making it impossible to hold a statistically significant quantity core for experimentation. Prior art requires use of native core which is not readily available resulting in lack of a statistically significant population of sample.

Additional prior art is represented in a technical paper titled "Effect of Pressure on Imbibition in Shale Oil Reservoirs with Wettability Considered" by Jiawei Tu and James J. Sheng, Energy Fuels 2020, 34, 4, 4260-4272 Publication Date Mar. 2, 2020.

Therefore, it is desirable to provide a test method that allows for measurement of the ability of a holistic fracturing fluid and/or individual components to interact with unconventional shale oil and gas resource rocks to improve upon the wettability and subsequent fluid imbibition and oil displacement mechanism in those rocks. The above discussed limitations in the prior art are not exhaustive. The current invention provides an inexpensive, time saving, more reliable apparatus and method of using the same where the prior art fails.

SUMMARY OF THE INVENTION

In view of the foregoing disadvantages inherent in the known types of evaluating spontaneous hydraulic fracturing fluid imbibition and oil displacement tests method and apparatus now present in the prior art, the present invention provides a new and improved test apparatus, system, and method. As such, the general purpose of the present invention, which will be described subsequently in greater detail, is to provide a new and improved test apparatus, system, and method of using the same, which has all the advantages of the prior art devices and none of the disadvantages.

To attain this, the present invention essentially comprises utilizing a composite core that is made from drill cuttings, utilizing a pressure cell for holding core and fluids to be tested that can be rated for a pressure range of 0 PSI to 10,000 PSI, utilizing a high pressure generator, simulating fracture faces encountered in hydraulic fracturing operations wherein imbibition forces of the fluid interact with the rock at all possible angles further simulating hydraulic fracturing operations, pressurizing the fluid into the core to the preferred embodiment pressure of 500 PSI, placing the cells into a roller oven custom designed to the pressure cell size for heating to evaluate under formation temperature conditions, combinations thereof, and so forth.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in this application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception upon which this disclosure is based may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

Therefore, it is an object of the present invention to provide a new and improved evaluation of spontaneous hydraulic fracturing fluid imbibition and oil displacement apparatus, system, and method of using the same, which may provide a test method that allows for measurement of the ability of a holistic fracturing fluid and/or individual components to interact with unconventional shale oil and gas resource rocks to improve upon the wettability and subsequent fluid imbibition and oil displacement mechanism in those rocks.

It is a further object of the present invention to provide a new and improved evaluation of spontaneous hydraulic fracturing fluid imbibition and oil displacement apparatus, system, and method of using which may be easily and efficiently manufactured and marketed.

An even further object of the present invention is to provide a new and improved evaluation of spontaneous hydraulic fracturing fluid imbibition and oil displacement apparatus, system, and method of using same, which is susceptible to a low cost of manufacture with regard to both materials and labor, and which accordingly is then susceptible to low prices of sale to the consuming industry, thereby making such value economically available to those in the field.

Still another object of the present invention is to provide a new and improved evaluation of spontaneous hydraulic fracturing fluid imbibition and oil displacement apparatus, system, and method of using, which provides all of the advantages of the prior art, while simultaneously overcoming some of the disadvantages normally associated therewith.

Another object of the present invention is to provide a new and improved evaluation of spontaneous hydraulic fracturing fluid imbibition and oil displacement apparatus, system, and method of using the same that is effective for 100 nanodarcies to 10 millidarcies permeability rocks that characterize unconventional oil and gas shale resources.

Yet another object of the present invention is to provide a new and improved evaluation of spontaneous hydraulic fracturing fluid imbibition and oil displacement apparatus, system, and method of using that provides fast spontaneous fracturing fluid imbibition and oil displacement testing on core in a very low cost apparatus that does not require a PLC or electricity to operate.

An even further object of the present invention is to provide a new and improved evaluation of spontaneous hydraulic fracturing fluid imbibition and oil displacement apparatus, system, and method of using the same that provides imbibition time that is 3 days as compared to months in prior art.

Still another object of the present invention is to provide a new and improved evaluation of spontaneous hydraulic fracturing fluid imbibition and oil displacement apparatus, system, and method of using that allows fluids to be further evaluated under formation temperature conditions allowing evaluations of fluid breakdown properties caused by heat.

Yet still another object of the present invention is to provide a new and improved evaluation of spontaneous hydraulic fracturing fluid imbibition and oil displacement apparatus, system, and method of using that can hold eleven each 1.5 inch diameter cores with an original oil in place of 62.7 ml wherein providing the quantity of original oil in place to be a larger volume than prior art thereby making the fluid oil displacement differentiation much easier to determine.

These, together with other objects of the invention, along with the various features of novelty which characterize the invention, are pointed out with particularity in the claims annexed to and forming a part of this disclosure. For a better understanding of the invention, its operating advantages, and the specific objects attained by its uses, reference should be had to the accompanying drawings and descriptive matter in which there are illustrated preferred embodiments of the invention.

BRIEF DESCRIPTION OF THE PICTORIAL ILLUSTRATIONS, GRAPHS, DRAWINGS, AND APPENDICES

The invention will be better understood and objects other than those set forth above will become apparent when consideration is given to the following detailed description thereof. Such description makes reference to the annexed pictorial illustrations, graphs, drawings, and appendices wherein.

DETAILED DESCRIPTION OF THE PREFERRED EMBODIMENTS

Figure 1:
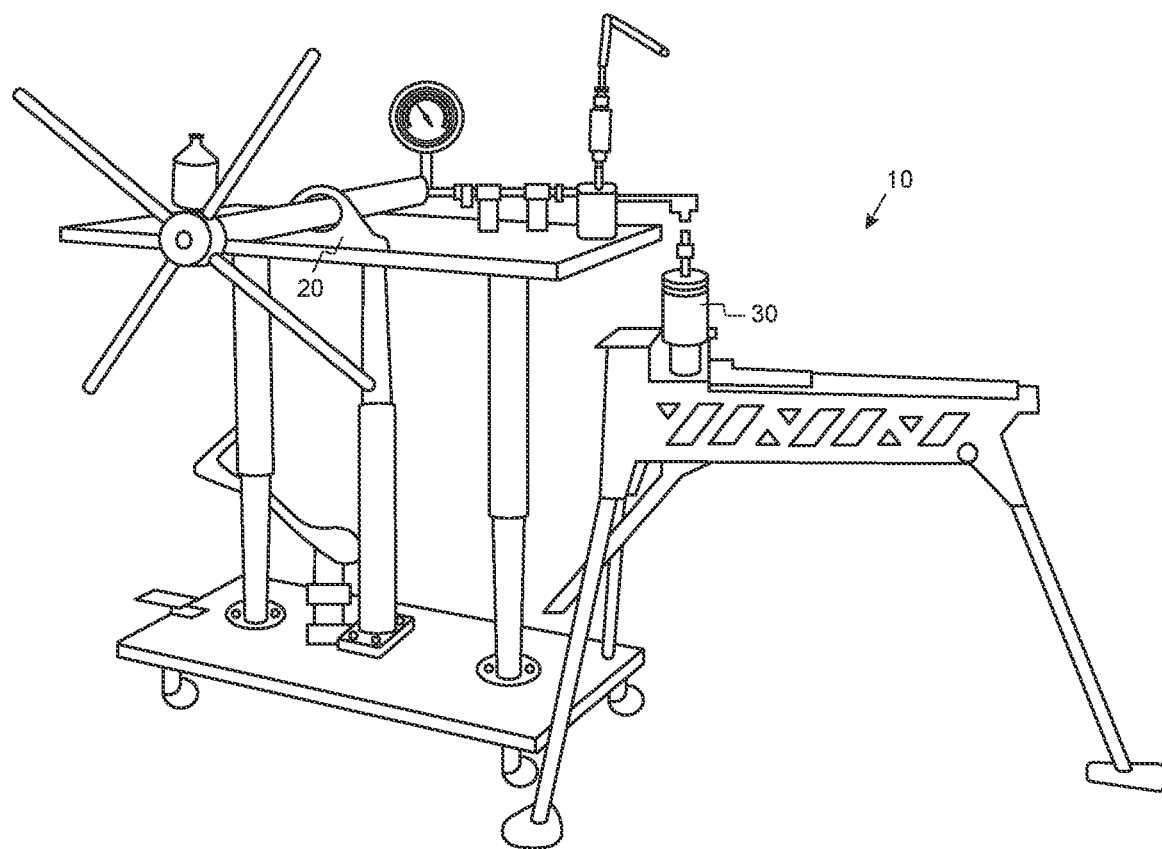
FIG. 1 is a general illustration of a preferred embodiment of the invention.
Figure 2:
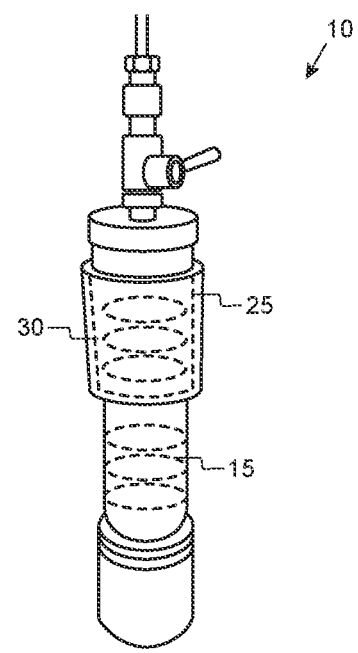
FIG. 2 is a general illustration of a preferred embodiment of the invention.
Figure 3:
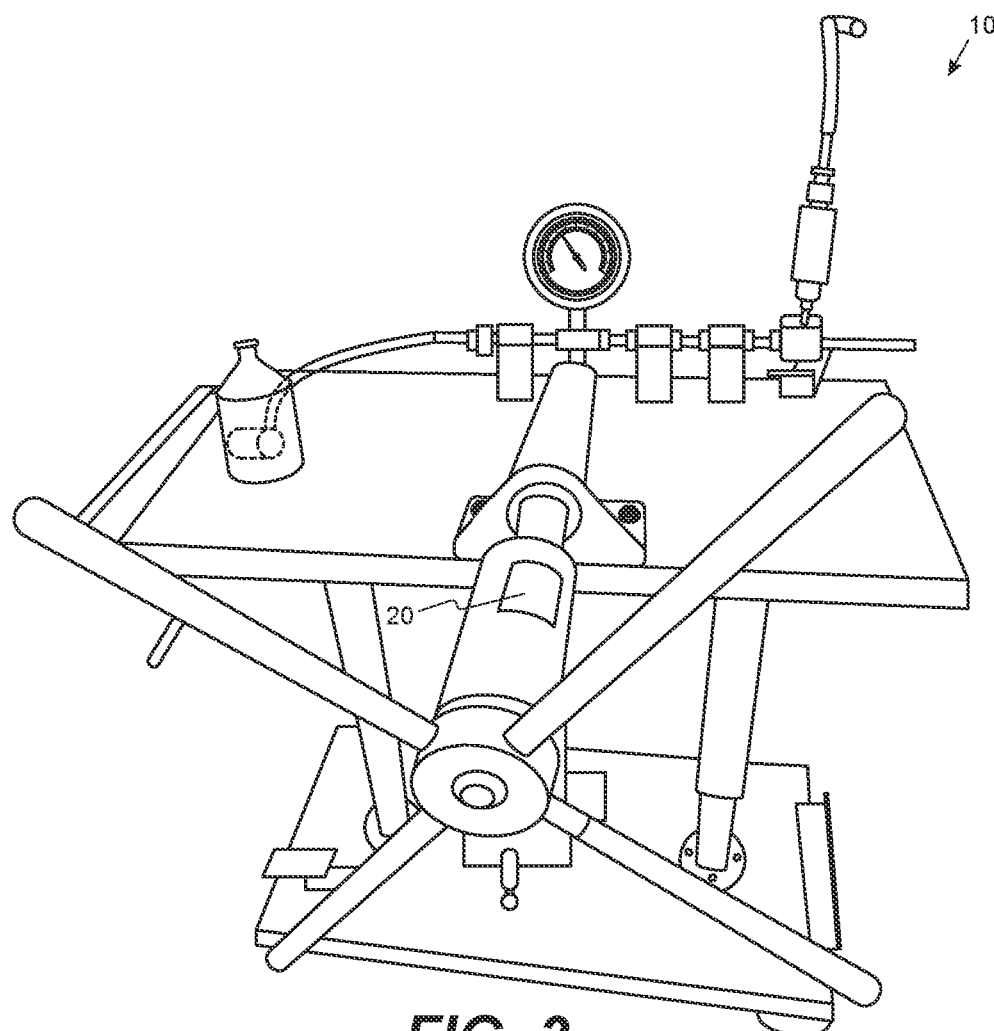
FIG. 3 is a general illustration of a preferred embodiment of the invention.
Figure 4:
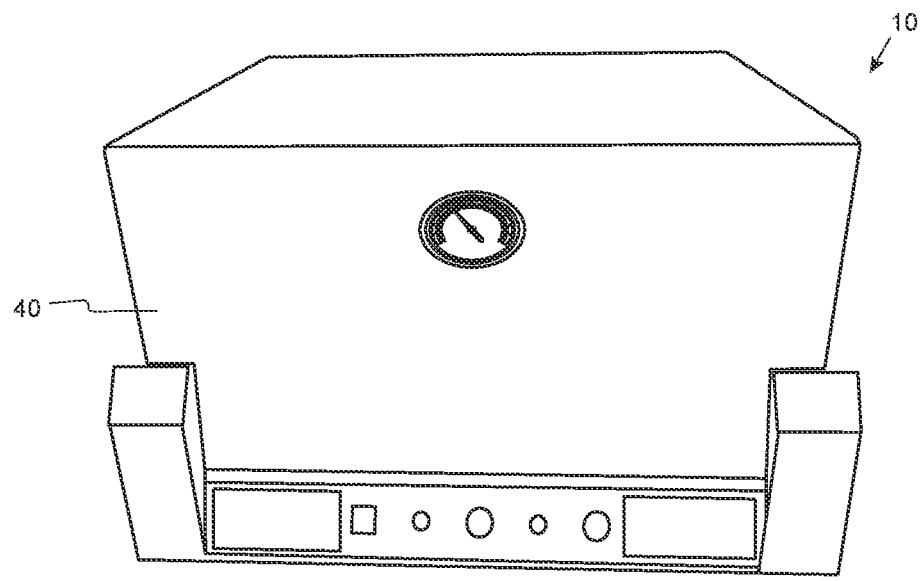
FIG. 4 is a general illustration of a preferred embodiment of the invention.

Referring to the illustrations, drawings, and pictures, reference character 10 generally designates a new and improved test, apparatus, method, and system that allows for measurement of the ability of a holistic fracturing fluid and/or individual components to interact with unconventional shale oil and gas resource rocks to improve upon the wettability and subsequent fluid imbibition and oil displacement mechanism in those rocks. Invention 10 is generally used in conjunction with well fracturing for the retrieval of hydrocarbons below the surface. It is contemplated that invention 10 may be utilized for other well applications other than hydrocarbon retrieval such as but not limited to water retrieval.

Invention 10 may utilize a composite core 15 that is made from drill cuttings. The cuttings are oil saturated by homogenous kneading and placed into a compactor device that can make a core of varied porosity that ranges from 5% porosity to 20% porosity with the preferred embodiment being that composite core 15 porosity results in pore space that holds 5.7 ml of oil per 57 mg of cuttings. Thus, invention 10 overcomes prior art where native core is required. Invention 10 renders limited sample availability as a non-issue. Pumped oil saturation of the core as is required with native core is avoided and damage related issues are eliminated. Composite core 15 samples can be simultaneously created and oil saturated in minutes making evaluation of hundreds to thousands of hydraulic fracturing fluid combinations possible.

Invention 10 utilizes a pressure cell 30 for holding core 15 and fluids 25 to be tested that can be rated for a pressure range of 0 PSI to 10,000 PSI with the preferred embodiment being 0 PSI to 1371 PSI at 200° Fahrenheit. Invention 10 preferred embodiment test method fluid imbibition pressure is 500 PSI. Invention 10 pressure cell 30 preferred embodiment inside diameter is 2" and length is 11.5 inches. Other size and pressure rating configurations are possible. Invention 10 preferred embodiment can hold eleven each 1.5 inch diameter cores 15 with an original oil in place of 62.7 ml. The quantity of original oil in place is a much larger volume than prior art, typically 10 ml, that makes fluid oil displacement differentiation much easier to determine. One inch length by 1.5 inch diameter composite cores 15 are stacked in invention 10 pressure cell 30 and simulate fracture faces encountered in hydraulic fracturing operations. Imbibition forces of the fluid interact with the rock at all possible angles further simulating hydraulic fracturing operations.

In a preferred embodiment, pressure generator 20 may be a HIGH PRESSURE EQUIPMENT COMPANY MODEL #112-5.75-5 pressure generator although other embodiments are possible. The simplistic design of the preferred embodiment results in faster cleaning times, less risk of air entrainment, elimination of electrical requirements, and full operator pressure control as compared to other pumping options.

Once the pressure cell 30 is loaded with the core 15 and fluid 25 to be tested, invention 10 pressurizes the fluid 25 into the core 15 to the preferred embodiment pressure of 500 PSI. The entire process takes minutes as compared to days and months with prior art. Throughput is only limited by the number of pressure cells 30 available.

In a preferred embodiment, invention 10 imbibition time is 3 days as compared to months in prior art. Fluids 25 can further be evaluated under formation temperature conditions by placing the cells 30 into a roller oven 40 custom designed to the pressure cell 30 size for heating. Benefits of heating the pressure cells 30 are that fluid 25 breakdown properties caused by heat can optionally be evaluated.

Invention 10 contemplates a method for evaluating spontaneous hydraulic fracturing fluid imbibition and oil displacement comprising the steps: providing at least 10 composite cores made from drill cuttings ranges from 5% porosity to 20% porosity with an original oil in place of 62.7 ml; providing a pressure cell for holding said at least 10 composite cores and fluids to be tested with a pressure range of 0 PSI to 10,000 PSI with said fluid imbibition pressure is about 500 PSI; simulating fracture faces encountered in a hydraulic fracturing operations wherein imbibition forces of said fluid interact with at least 10 composite cores at all possible angles by pressurizing said pressure cell; providing said imbibition in 3 days; and evaluating spontaneous hydraulic fracturing fluid said imbibition and said oil displacement.

Changes may be made in the combinations, operations, and arrangements of the various parts and elements described herein without departing from the spirit and scope of the invention. Furthermore, names, titles, headings and general division of the aforementioned are provided for convenience and should, therefore, not be considered limiting.

I claim:

1. A method for evaluating spontaneous hydraulic fracturing fluid imbibition and oil displacement comprising the steps:
   providing at least 10 composite cores made from drill cuttings ranges from 5% porosity to 20% porosity with an original oil in place of 62.7 ml;
   providing a pressure cell for holding said at least 10 composite cores and fluids to be tested with a pressure range of 0 PSI to 10,000 PSI with said fluid imbibition pressure is 500 PSI;
   simulating fracture faces encountered in a hydraulic fracturing operations wherein imbibition forces of said fluid interact with at least 10 composite cores at all possible angles by pressurizing said pressure cell; and
   evaluating spontaneous hydraulic fracturing fluid said imbibition and said oil displacement.

* * * * *